United States Patent [19]
Robinson et al.

[11] 3,993,050
[45] Nov. 23, 1976

[54] SPIROMETER

[75] Inventors: Thomas C. Robinson; Sotiris Kitrilakis, both of Berkeley, Calif.

[73] Assignee: Searle Cardio-Pulmonary Systems Inc., Emeryville, Calif.

[22] Filed: May 19, 1975

[21] Appl. No.: 578,528

[52] U.S. Cl. ............................................. 128/2.08
[51] Int. Cl.² ........................................... A61B 5/08
[58] Field of Search ............ 128/2.07, 2.08; 222/95, 222/96; 35/17

[56] References Cited
UNITED STATES PATENTS

| | | | |
|---|---|---|---|
| 3,561,644 | 2/1971 | Works | 222/95 |
| 3,562,924 | 2/1971 | Baermann | 35/17 |
| 3,810,461 | 5/1974 | McCormick | 128/2.08 |
| 3,889,660 | 6/1975 | Kitrilakis | 128/2.08 |

Primary Examiner—Harland S. Skogquist
Attorney, Agent, or Firm—Lothrop & West

[57] ABSTRACT

A spirometer has a housing with a wall having an opening therein. A bag made up of a first, stiff sheet and a second, flexible sheet having an exhaust slit therein as well as an inlet tube is supported within the housing with the first sheet lying against the wall and with the inlet tube extending through the opening. A valve flap within the bag overlies the inlet tube and a valve bar in the housing is spring urged with a selected force to press the bag, between the slit and the tube, against the wall. A primary plate is hinged to the housing at its top to lie against the second sheet. A secondary plate is similarly hinged and is power controlled to be spaced from or to press against the primary plate through an intervening cushion. The position of the primary plate is indicated mechanically and also by electrical instrumentation.

6 Claims, 8 Drawing Figures

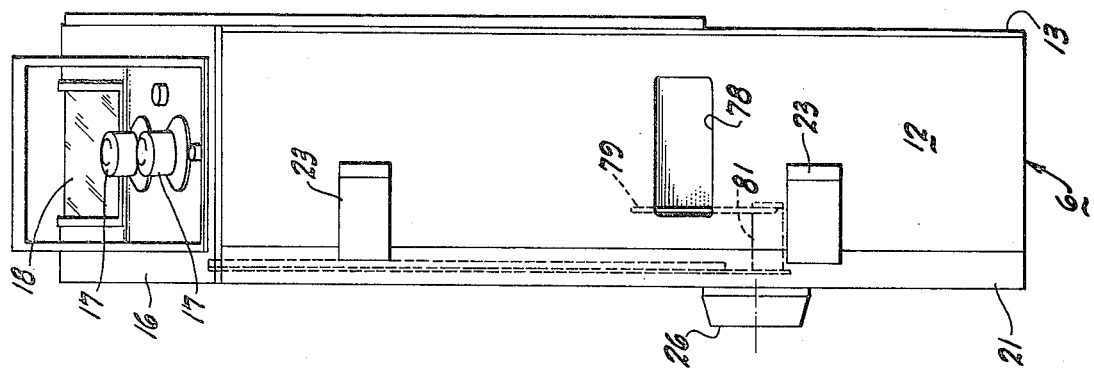
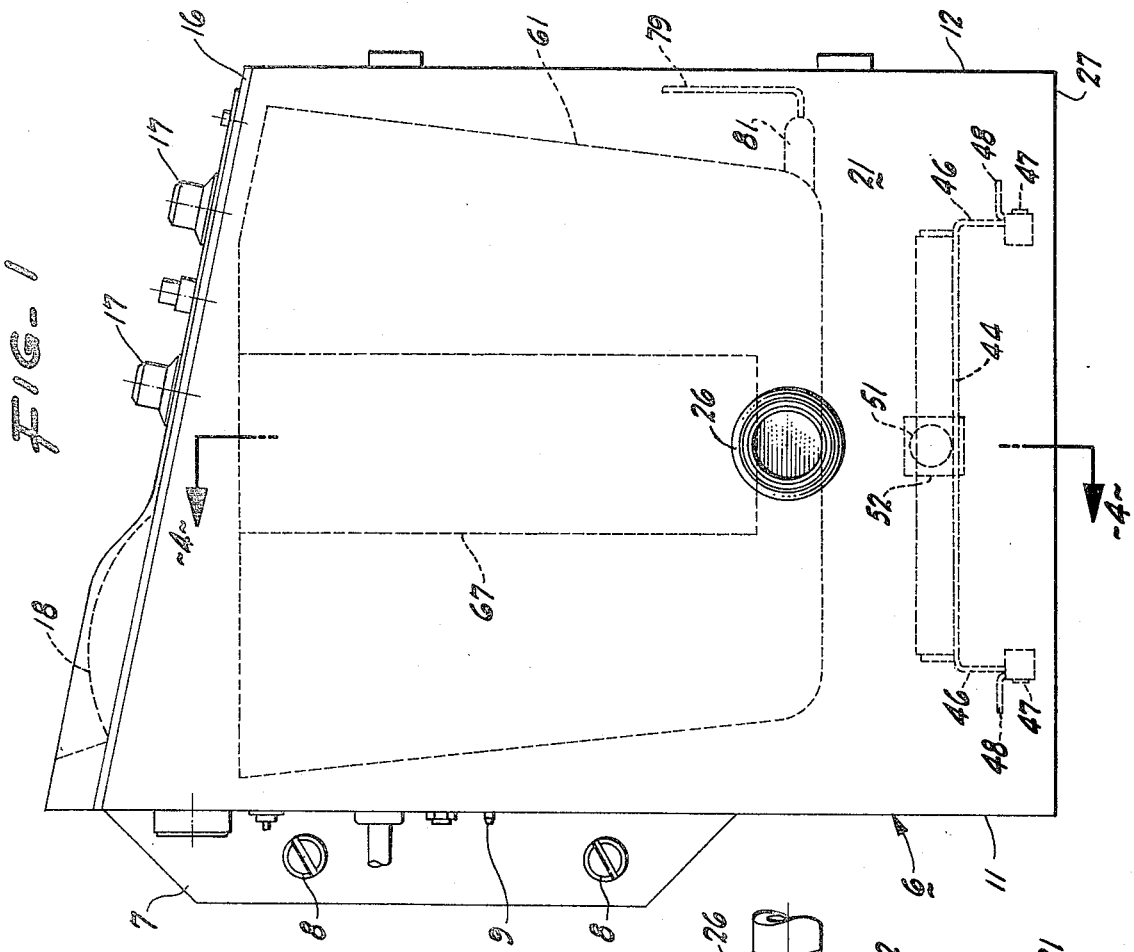
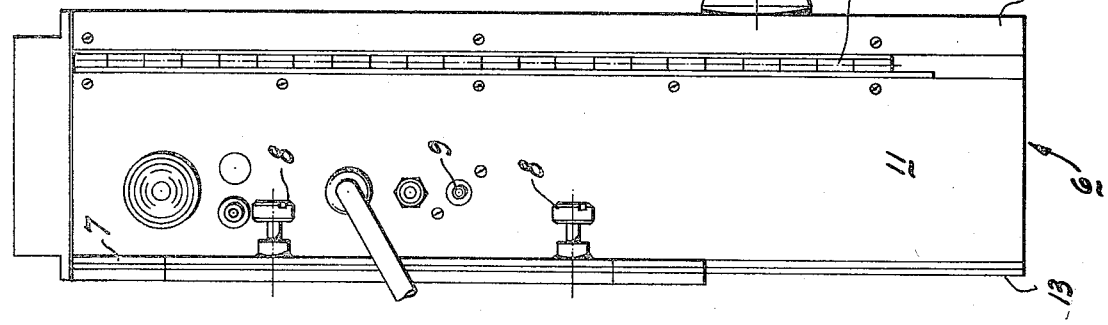

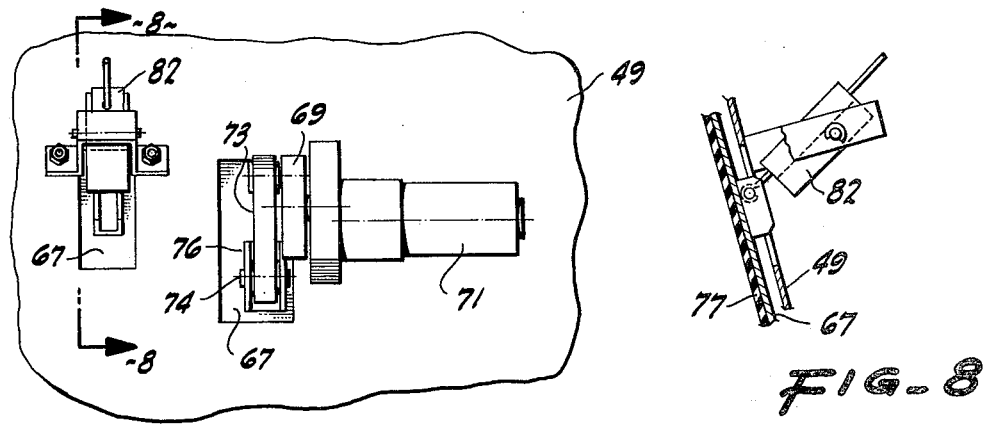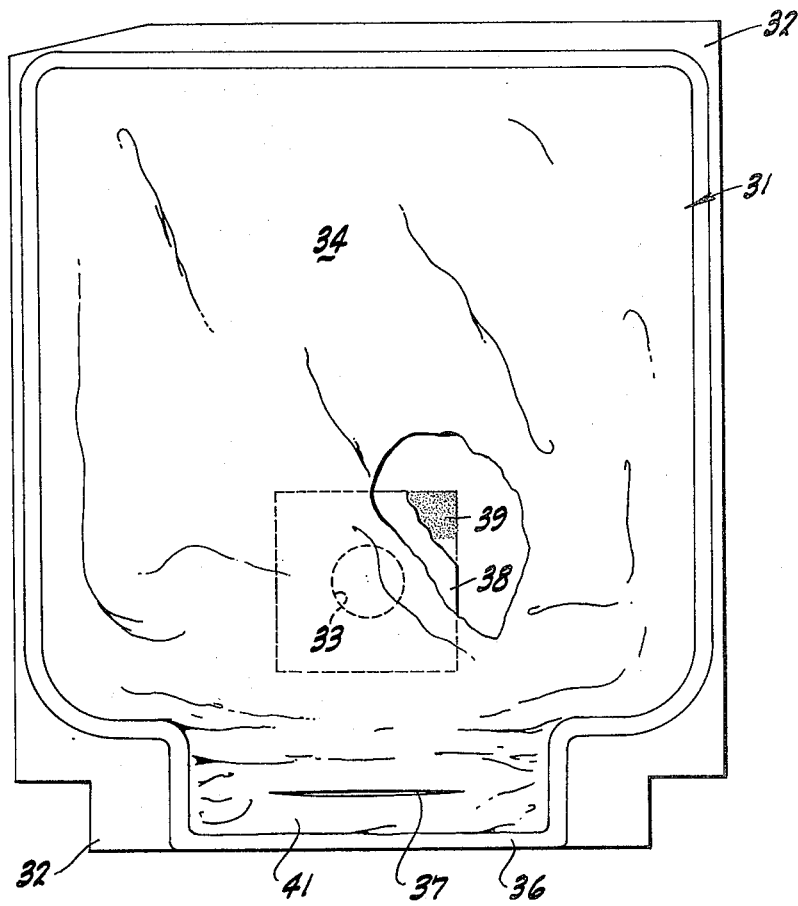

3,993,050

SPIROMETER

The disclosure herein is related to that in the pending application of Sotiris Kitrilakis entitled "Spirometer" filed Oct. 4, 1973 with Ser. No. 403,467, Now U.S. Pat. No. 3,889,660 issued June 17, 1975 and assigned to the assignee hereof.

The earlier spirometer, just identified, acts to afford an indication of the volume of an exhaled breath from a patient being observed. The volume of breath is the important criterion and pressure is not consequential since, with that spirometer, there is only a small pressure variation during breathing. The earlier spirometer as well as this one are particularly designed for use in conjunction with a respirator of the sort shown in U.S. Pat. No. 3,840,006 issued Oct. 8, 1974 to Keith E. Buck, Sotiris Kitrilakis and Thomas C. Robinson and also assigned to the assignee hereof.

It is an object of the present invention to provide a spirometer which is generally an improvement over the spirometer above mentioned and other spirometers now generally available.

Another object of the invention is to provide a very simple spirometer well adapted for use with replaceable breathing bags so that sanitation can be strictly maintained.

Another object of the invention is to provide a spirometer which can readily be observed in operation.

A further object of the invention is to provide a spirometer in which the working of the mechanism is light and easy so as to impose only an insignificant breathing load on the exhaling patient.

A further object of the invention is to provide a spirometer that is mechanically simple, readily cared for and effective in its working.

A further object of the invention is in general to provide an improved spirometer.

Other objects of the invention, together with the foregoing, are attained in the embodiment thereof described in the accompanying description and illustrated in the accompanying drawings, in which:

FIG. 1 is a side elevation of a spirometer constructed pursuant to the invention, the positioning of some interior mechanism being illustrated by broken lines;

FIG. 2 is a front elevation of the structure shown in FIG. 1;

FIG. 3 is a rear elevation of the structure of FIG. 1;

FIG. 6 is a side elevation, to a reduced scale, of the bag shown in FIG. 5;

FIG. 7 is a detailed view showing some of the mechanism as seen from a plane indicated by the line 7—7 in FIG. 4; and FIG. 8 is a side elevation of some of the mechanism shown in FIG. 7, the plane of the view being illustrated by the line 8—8 of FIG. 7.

Figure 4:
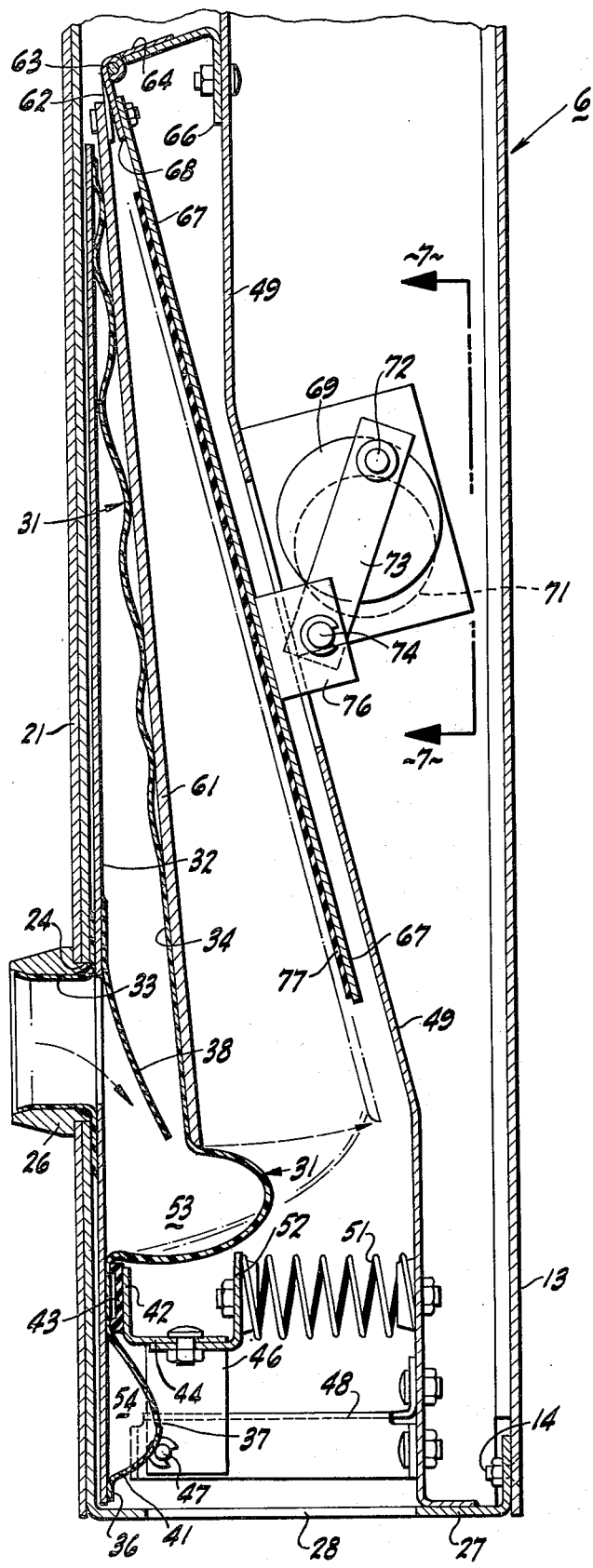
FIG. 4 is a cross-section, the plane of which is indicated by the line 4—4 of FIG. 1.

The spirometer is particularly inclusive of a housing 6 or frame (FIG. 1) having a mounting bracket 7 and fastenings 8. In most instances the spirometer is utilized in connection with a volume ventilator, as indicated above, to which the fastenings 8 are readily secured. While the spirometer is in most respects a separate unit, it can be supported on and closely related to the ventilator and can have a pneumatic signal connection 9 therewith. The housing 6 has fixed side panels 11 and 12, a readily removable rear panel 13 (FIG. 4) fastened in position by bolts 14, and a top panel 16 having various controls 17 thereon as well as an electrical indicator 18. The housing also has a flanged front panel 21 supported by a hinge 22 (FIG. 3) and normally held in closed position by toggle fasteners 23 effective when closed to secure the front panel firmly in position with respect to the remainder of the housing. The front panel 21 at a convenient location is provided with an opening 24 bounded by a permanent grommet 26. The bottom panel 27 of the housing is particularly provided with an opening 28. This affords communication between the interior of the housing and the atmosphere.

Figure 5:
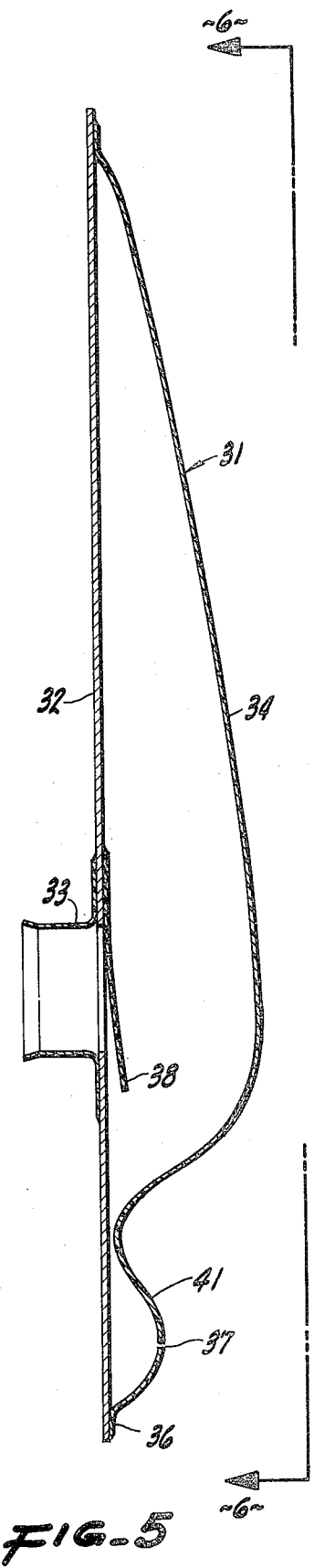
FIG. 5 is a cross-section of a bag, as shown in FIG. 4 but removed from the surrounding structure.

Forming part of the spirometer but arranged to be utilized but once therein and then replaced is a bag 31 (FIGS. 4 and 5). The bag is made up of a number of parts particularly including a first relatively stiff or rigid sheet 32 of inexpensive, air-tight material, such as cardboard, having approximately a rectangular outline and normally being flat. The first sheet 32 has an open tube 33 thereon designed approximately to register with and to extend through the opening 24. Secured all around its edges to the first sheet 32 is a second, flexible sheet 34. This is of a heat formable material and can fold, wrinkle and distort substantially.

The sheet 34 is considerably larger in area than the sheet 32 but is fixed around its edges to the edges of the sheet 32. It is thus confined generally within the confines of the sheet 32. Yet, the sheet 34 has sufficient extra material so that it can be deformed to lie against the first sheet for storage, packing and the like and can also be expanded or ballooned substantially to afford a commodious container.

The sheet 34 is generally uninterrupted except that near a lower edge 36 but spaced above such edge the second sheet is provided with a narrow slit 37 (FIG. 6). The slit 37 normally is substantially closed by the relaxed resiliency of the sheet 34 but can open due to pressure within the bag to afford release of fluid from the bag interior. In addition, the bag is provided interiorly with a flexible flap 38 joined along one edge to the first sheet 32 by an appropriate strip 39 of adhesive. The flap otherwise is free. When relaxed the flap 38 lies closely adjacent the stiff sheet 32 and seals the tube 33 but when there is flow inwardly through the opening of the tube 33, the resilient flap is displaced into an open position comparable to that shown in FIG. 5. Although the bag is generally rectangular, it can have a reduced lower portion 41, as shown in FIG. 6, in order particularly to accommodate itself to the shape and configuration of the housing.

To isolate one portion of the bag from another portion there is afforded a valve bar 42 carrying a relatively soft contactor 43 adapted to abut a specially provided area of the reduced portion 41 of the bag. The valve bar is mounted at the upper end of a lever 44 having downturned legs 46 arranged to pivot on pins 47 projecting from angle brackets 48 secured to an intermediate frame wall 49 extending generally vertically from the bottom to the top of the housing (FIG. 5).

The lever 44 is particularly urged in one direction by a calibrated spring 51 having one end positioned against the intermediate wall 49 and having its other end against a tab 52 upstanding from the lever 44. The spring normally urges the resilient or soft face of the contactor bar 43 against the positioned bag and forces the second, flexible sheet 34 against the stiff sheet 32 and thus isolates the portion of the bag in the vicinity of the slit 37 from the portion of the bag thereabove and in the vicinity of the tube 33. In this fashion there is provided an upper volume 53 and an isolated lower volume 54. The resilient face of the bar 43 makes a substantially air-tight seal between the volumes 53 and 54 of the bag.

Designed to rest by gravity against the bag, particularly the flexible second sheet 34 thereof, is a primary plate 61, having a somewhat trapezoidal shape in face elevation, and at its upper end being secured to a hinge leaf 62 joined by a pivot or hinge rod 63 to another hinge leaf 64 secured by a bracket 66 to the upper end of the intermediate wall 49. The primary plate 61 is thus free to rest by gravity against the side of the bag and is also free to be lifted away from the front panel or wall 21.

Supplementing the primary plate is a secondary plate 67 depending from a hinge leaf 68 having the same hinge rod 63 and thus supported from the bracket 66 to swing on the same axis as the primary plate 61. The secondary plate 67 is free to move in an arc but under the mechanical control of a rotating disc 69 driven by a motor 71, as described in the above-identified spirometer application, and under control of appropriate mechanism. The disc 69 has a crank pin 72 projecting therefrom and joined by a connecting bar 73 to a pin 74 disposed in a bracket 76 secured to the secondary plate 67.

Under many conditions the motor driven parts are held stationary in the position shown in FIG. 4 and the plate 67 is spaced from the plate 61. Upon occasion, when the motor 71 is energized, the crank pin 72 makes one complete rotation and moves the secondary plate 67 through one full cycle, first to approach the front wall 21 and then to return to the indicated position. The secondary plate 67 is provided on one face with a soft, resilient cushion 77. Movement or position of the secondary plate is indicated, as shown in the identified application, by the electric meter 18. Also, the momentary position of the primary plate 61 is discernable through a window 78 (FIG. 2) cut in the side wall 12 and revealing an indicator needle 79 carried by a bracket 81 secured to the bottom portion of the primary plate 61.

In the operation of this mechanism the spirometer casing is appropriately mounted and connected as described and the fasteners 23 are released and the front panel 21 is swung open. A bag 31 is positioned within the housing with the inlet tube 33 thereon extending into and substantially through the opening 24 and the grommet 26. In this position the stiff, first sheet 32 tends to rest against the bottom flange of the front panel 21 and by that abutment and the interengagement of the inlet tube 83 and the front panel, the bag is well supported in the housing. With the bag so supported the door front panel is swung shut and the fasteners 23 are toggled into closed position. The closing action brings the inner flexible sheet 34 into abutment with the valve bar face 43. The device is then hooked up by a patient's breathing tube to the patient directly or through a volume ventilator and is appropriately electrically energized.

With the parts in the position shown in FIG. 4, when the patient exhales, his incoming breath displaces the flap valve 38 and causes the bag 31 to distend by flexure of the flexible second sheet 34. The distending bag simultaneously swings the primary plate 61 counterclockwise or toward the right, at the bottom of FIG. 4, about the hinge rod 63 as an axis. The distension of the bag does not occur in the lower volume 54 thereof since the valve 43 prevents any fluid ingress to the volume 54. As the primary plate 61 moves, its motion is translated by a linear potentiometer 82 (FIG. 7) and causes an indication on the meter 18. At the same time, the motion of the primary plate is observable by the concurrent displacement of the needle 79 as seen through the window 78 so that anyone passing can at a glance observe that the device is functioning.

When the primary plate 61 has been displaced a maximum amount by the patient's exhalation and when the exhalation has stopped, the valve 38 closes due to its resiliency and lack of unbalanced pressure thereon, and traps the exhaled breath within the bag volume 53. At about that time the motor 71 is energized and the secondary plate 67 is moved to abut the primary plate 61 through the cushion 77. Further secondary plate movement by motor power forces the primary plate to rotate in a clockwise direction, or to the left in FIG. 4, thus increasing the pressure within the bag. The pressure increase is sufficient to distort the bag and so to rock the lever 44 about the pins 47 and against the urgency of the spring 51 to move the flexible sheet 34 away from the stiff sheet 32.

The spring 51 is particularly calibrated so that its force is sufficient to keep the valve bar 42 closed when the patient is exhaling, but is insufficient to keep the valve bar closed when the bag is being deflated under the mechanical action of the secondary plate 67 and the motor. The content of the bag is, therefore, displaced past the face 43 of the opened valve bar and flows into the volume 54 from which it escapes through the slit 37 distorted open by the outflowing fluid.

The discharged breath continues to the atmosphere through the opening 28. Since the slit 37 is above the bottom of the volume 54, there remains a space for the accumulation of material otherwise carried by the breath, such as moisture and the like from the patient. This is retained by gravity in the bag and is not normally discharged to the atmosphere. The cycle just described continues indefinitely. When it is desired to put another patient on the spirometer or otherwise to change the situation, the power is discontinued, the door panel 21 is opened and the bag 31 is removed and thrown away. A replacement bag of similar construction is put into position and the machine is ready for further functioning.

What is claimed is:

1. A spirometer comprising a housing having a side wall with an opening therein, a bag defined on one side by a first stiff sheet and defined on the opposite side by a second flexible sheet, said bag having a slit therein, an inlet tube in said bag, means including a bottom wall in said housing for supporting said first stiff sheet of said bag in said housing adjacent said side wall with said inlet tube extending through said opening, a valve flap in said bag overlying said tube, a valve bar, means for mounting said bar in said housing for movement toward and away from abutment with said bag between said slit and said tube, yieldable means for urging said bar toward said bag, a primary plate, means for mounting said primary plate in said housing for movement toward and away from said bag, a secondary plate, means for mounting said secondary plate in said housing for movement toward and away from abutment with said primary plate, and means in said housing for so moving said secondary plate.

2. A device as in claim 1 in which said means for mounting said bar includes a lever pivoted on said housing and in which said means for urging said bar toward said bag is a spring engaging said lever and said housing, said spring having a force opposed by pressure in said bag due to movement of said secondary plate by said moving means.

3. A device as in claim 1 in which said yieldable means is a spring strong enough to urge said valve bar against said bag during patient exhalation and weak enough to yield when said bag is collapsed under force from said secondary plate.

4. A bag subcombination comprising a relatively stiff first sheet having an opening, an inlet tube mounted on said first sheet and projecting therefrom in substantial registry with said opening, a flexible flap valve secured to said first sheet and adapted yieldably to overlie said opening, a flexible second sheet, means for securing the periphery of said second sheet to the periphery of said first sheet, and means defining a normally closed air slit in said second sheet, said second sheet being sufficiently flexible to distort and open said slit under superior pressure within said bag.

5. A bag subcombination as in claim 4 in which the lower edge of said second sheet is considered as the bottom when said sheet extends vertically and said means defining said air slit is spaced above said bottom a distance to leave a space for the gravity accumulation of material between the slit and said lower edge.

6. A bag subcombination as in claim 4 in which said second sheet has a larger surface area than said first sheet whereby said second sheet is free to expand flexibly with respect to said stiff first sheet.

* * * * *